(12) United States Patent
Eisinger

(10) Patent No.: US 11,253,255 B2
(45) Date of Patent: Feb. 22, 2022

(54) KNIFE LOCKOUT WEDGE

(71) Applicant: Covidien LP, Mansfield, MA (US)

(72) Inventor: Joseph Eisinger, Northford, CT (US)

(73) Assignee: Covidien LP, Mansfield, MA (US)

(*) Notice: Subject to any disclaimer, the term of this patent is extended or adjusted under 35 U.S.C. 154(b) by 73 days.

(21) Appl. No.: 16/890,150

(22) Filed: Jun. 2, 2020

(65) Prior Publication Data

US 2021/0022731 A1    Jan. 28, 2021

Related U.S. Application Data

(60) Provisional application No. 62/879,072, filed on Jul. 26, 2019.

(51) Int. Cl.
*A61B 17/02* (2006.01)
*A61B 17/115* (2006.01)
*A61B 17/068* (2006.01)
*A61B 17/072* (2006.01)

(52) U.S. Cl.
CPC ..... *A61B 17/0686* (2013.01); *A61B 2017/07228* (2013.01); *A61B 2017/07271* (2013.01); *A61B 2017/07285* (2013.01)

(58) Field of Classification Search
CPC .......... A61B 2017/07214; A61B 2017/07285; A61B 17/1155; A61B 17/072; A61B 17/115
USPC .................................................. 227/180.1
See application file for complete search history.

(56) References Cited

U.S. PATENT DOCUMENTS

| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |

(Continued)

FOREIGN PATENT DOCUMENTS

| CA | 908529 A | 8/1972 |
| CA | 2805365 A1 | 8/2013 |

(Continued)

OTHER PUBLICATIONS

Extended European Search Report issued in European Patent Application No. 20187315.5, dated Dec. 15, 2020.

*Primary Examiner* — Gloria R Weeks
(74) *Attorney, Agent, or Firm* — Carter, DeLuca & Farrell LLP

(57) ABSTRACT

A surgical stapling device includes an adaptor assembly and a reload assembly supported on a distal end portion of the adaptor assembly. The reload assembly includes a shell housing, a staple cartridge supporting staples, a staple pusher, a staple actuator, a knife carrier, and a locking member. The staple pusher is movable from a retracted position to an advanced position to eject the staples from the staple cartridge. The staple actuator is movable from a retracted position to an advanced position to move the staple pusher from its retracted position to its advanced position. The knife carrier is movable between a retracted position and an advanced position. The locking member is supported on the knife carrier. The locking member is configured to engage the staple actuator in its advanced position while engaging the knife carrier in its retracted position such that the locking member inhibits re-advancement of the knife carrier.

19 Claims, 10 Drawing Sheets

(56) References Cited

U.S. PATENT DOCUMENTS

| | | |
|---|---|---|
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |

(56) References Cited

U.S. PATENT DOCUMENTS

| | | |
|---|---|---|
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | | |
|---|---|---|---|
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,687,237 B2 * | 4/2014 | Komatsu ................. H04N 1/58 |
| | | 358/3.06 |
| 8,733,611 B2 | 5/2014 | Milliman |
| 9,023,014 B2 | 5/2015 | Chowaniec et al. |
| 9,038,882 B2 * | 5/2015 | Racenet .............. A61B 17/1155 |
| | | 227/180.1 |
| 9,055,943 B2 | 6/2015 | Zemlok et al. |
| 9,168,042 B2 * | 10/2015 | Milliman ............. A61B 17/068 |
| 9,186,141 B2 * | 11/2015 | Williams ......... A61B 17/07207 |
| 9,861,368 B2 * | 1/2018 | Racenet ........... A61B 17/07207 |
| 9,962,159 B2 | 5/2018 | Heinrich et al. |
| 10,426,470 B2 * | 10/2019 | Guerrera .......... A61B 17/07207 |
| 10,842,495 B2 * | 11/2020 | Zhou ................. A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |

(56) References Cited

U.S. PATENT DOCUMENTS

| | | |
|---|---|---|
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0340351 A1 | 11/2017 | Sgroi, Jr. |
| 2018/0125495 A1 | 5/2018 | Sgroi, Jr. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2614785 A2 | 7/2013 |
| EP | 2623042 A2 | 8/2013 |
| EP | 2754398 A2 | 7/2014 |
| EP | 2823774 A2 | 1/2015 |
| EP | 3649966 A1 | 5/2020 |
| EP | 3730067 A1 | 10/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

\* cited by examiner

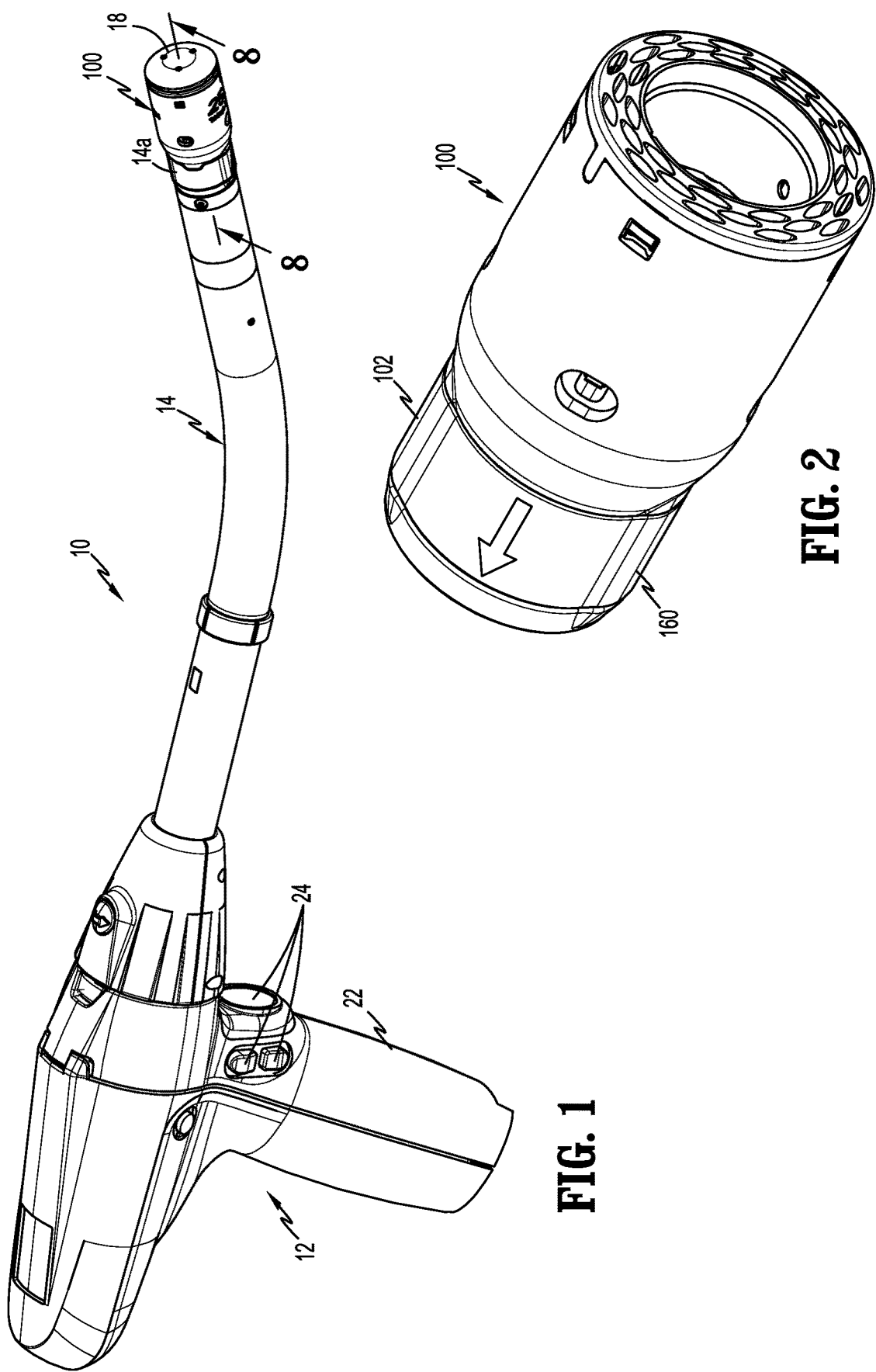

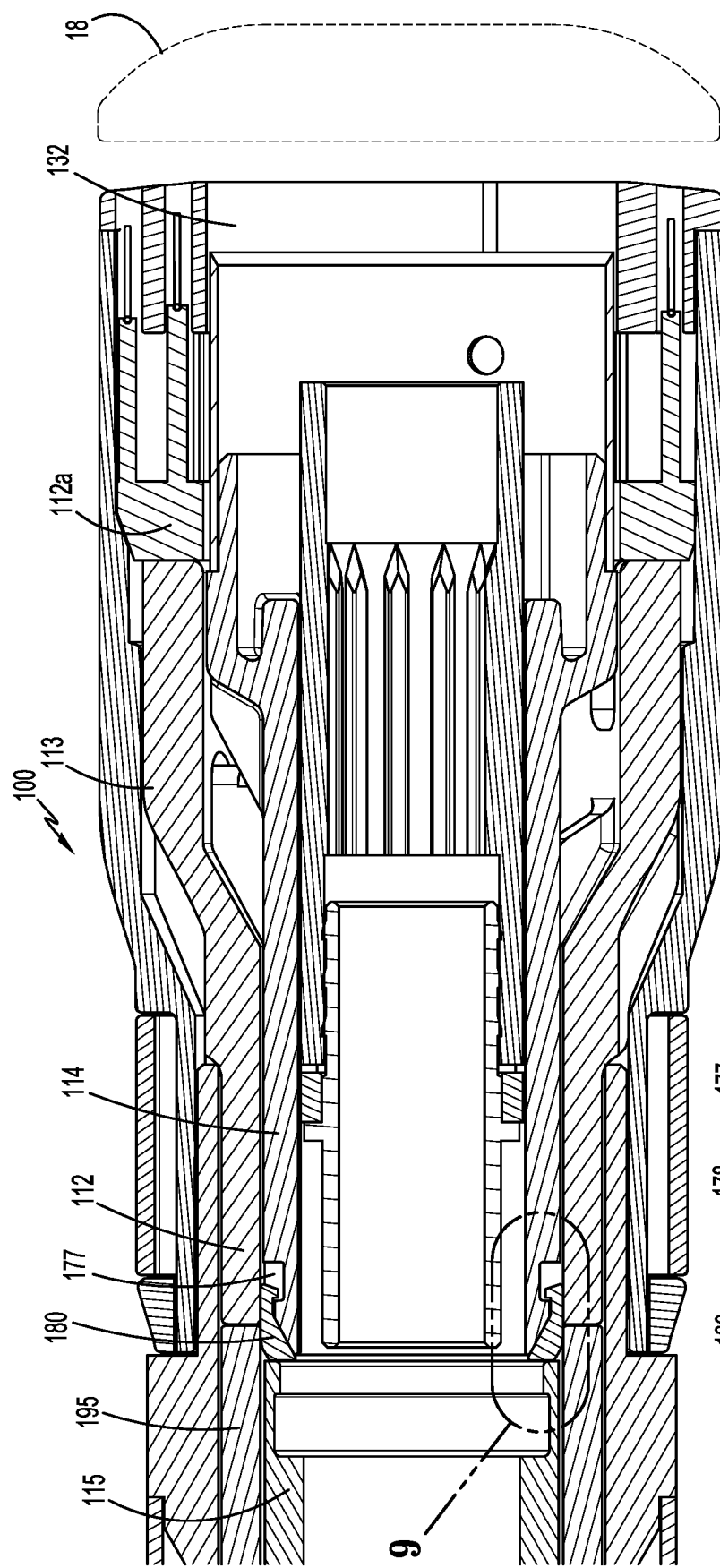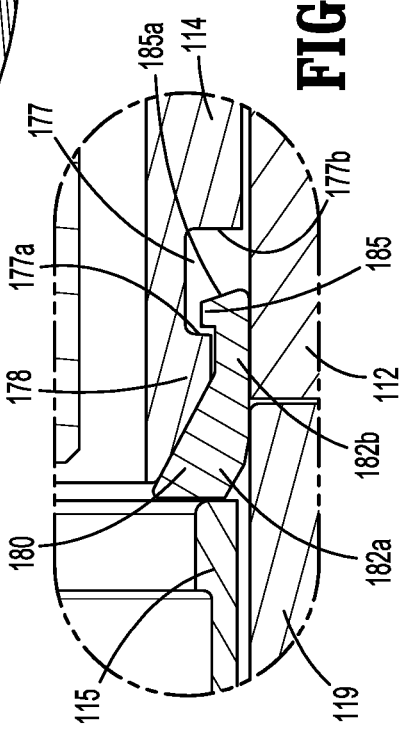

KNIFE LOCKOUT WEDGE

CROSS-REFERENCE TO RELATED APPLICATIONS

This application claims the benefit of and priority to U.S. Provisional Patent Application Ser. No. 62/879,072 filed Jul. 26, 2019, the entire disclosure of which is incorporated by reference herein.

BACKGROUND

Technical Field

The disclosure is directed to circular stapling devices and, more particularly, to reload assemblies for circular stapling devices with structure to retain a knife carrier of the reload assembly in a retracted position after the circular stapling device is fired.

Background of Related Art

Conventional circular stapling devices include an elongate body and a shell or reload assembly that is supported on a distal portion of the elongate body. The reload assembly includes a shell housing, a staple cartridge supported on the shell housing having a plurality of staples, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core or cut tissue.

After a circular stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

A continuing need exists in the art for a reload assembly that includes improved structure for retaining the knife/knife carrier in a retracted position.

SUMMARY

In accordance with an embodiment of the disclosure, a surgical stapling device includes an adaptor assembly having a proximal end portion and a distal end portion, and a reload assembly supported on the distal end portion of the adaptor assembly. The reload assembly includes a shell housing, a staple cartridge supporting a plurality of staples, a staple pusher, a staple actuator, a knife carrier, and a locking member. The shell housing includes an outer housing portion and an inner housing portion. The inner and outer housing portions define an annular cavity. The staple pusher is supported within the annular cavity and movable from a retracted position to an advanced position to eject the plurality of staples from the staple cartridge. The staple actuator is supported within the annular cavity and movable from a retracted position to an advanced position to move the staple pusher from its retracted position to its advanced position. The knife carrier is supported within the through bore and movable between a retracted position and an advanced position. The knife carrier supports a knife. The locking member is slidably supported on the knife carrier. The locking member is configured to engage the staple actuator in its advanced position while engaging the knife carrier in its retracted position such that the locking member inhibits re-advancement of the knife carrier.

In an embodiment, the knife carrier may have a proximal portion defining a circumferential groove configured to anchor the locking member thereagainst when the locking member engages the staple actuator is in its advanced position.

In another embodiment, the locking member may have an annular profile.

In yet another embodiment, the locking member may have a break for radial flexing thereof.

In yet another embodiment, the locking member may include proximal and distal portions. The proximal portion may have an engaging surface extending radially inward and a proximal surface defining an acute angle with the engaging surface.

In an embodiment, the distal portion of the locking member may include a hook portion.

In another embodiment, the knife carrier may include a plurality of longitudinally extending body portions. Adjacent longitudinally extending body portions may define a slot.

In yet another embodiment, the locking member may include an axial guide configured to be slidably received in the slot of the knife carrier.

In an embodiment, each longitudinally extending body portion may include a proximal portion defining a groove and a tapered portion proximal of the groove.

In another embodiment, the tapered portion of the longitudinally extending body portion may be configured to slidably engage the engaging surface of the locking member.

In another embodiment, the groove of the knife carrier may include a distal wall and a proximal wall. The hook portion of the locking member may include an engaging surface configured to slide over the distal wall of the groove.

In another embodiment, the proximal surface of the locking member may be configured to engage the proximal wall of the groove when the locking member engages the staple actuator in its advanced position.

In accordance with another embodiment of the disclosure, a surgical stapling device includes a reload assembly including a shell housing defining an annular cavity, a staple cartridge supporting a plurality of staples, a staple pusher, a staple actuator, a knife carrier, and a locking member. The staple pusher is supported within the annular cavity and movable from a retracted position to an advanced position to eject the plurality of staples from the staple cartridge. The staple actuator is supported within the annular cavity and engaged with the staple pusher. The staple actuator is movable from a retracted position to an advanced position to move the staple pusher from its retracted position to its advanced position. The staple actuator and the staple pusher define a through bore. The knife carrier is supported within the through bore and movable between a retracted position and an advanced position. The knife carrier includes a proximal portion defining a notch. The knife carrier supports a knife. The locking member is slidably supported on the knife carrier. The locking member includes an annular body having a proximal end configured to be anchored against the notch of the knife carrier and a distal end configured to engage the staple actuator such that when the staple actuator is in its advanced position and the knife carrier is in its retracted position, the locking member inhibits re-advancement of the knife carrier.

In an embodiment, a distal end of the locking member may be configured to slide over the notch of the knife carrier.

BRIEF DESCRIPTION OF THE DRAWINGS

Various aspects and features of the disclosure are described hereinbelow with reference to the drawings wherein like numerals designate identical or corresponding elements in each of the several views and:

FIG. 1 is a side perspective view of a circular stapling device including an exemplary embodiment of a disclosed reload assembly with the circular stapling device in a clamped position;

FIG. 2 is a side perspective view of the reload assembly of the circular stapling device shown in FIG. 1;

FIG. 8 is a cross-sectional view taken along section line 8-8 of FIG. 1 with the reload assembly in a pre-fired state;

FIG. 9 is an enlarged view of the indicated area of detail shown in FIG. 8;

DETAILED DESCRIPTION

Figure 3:
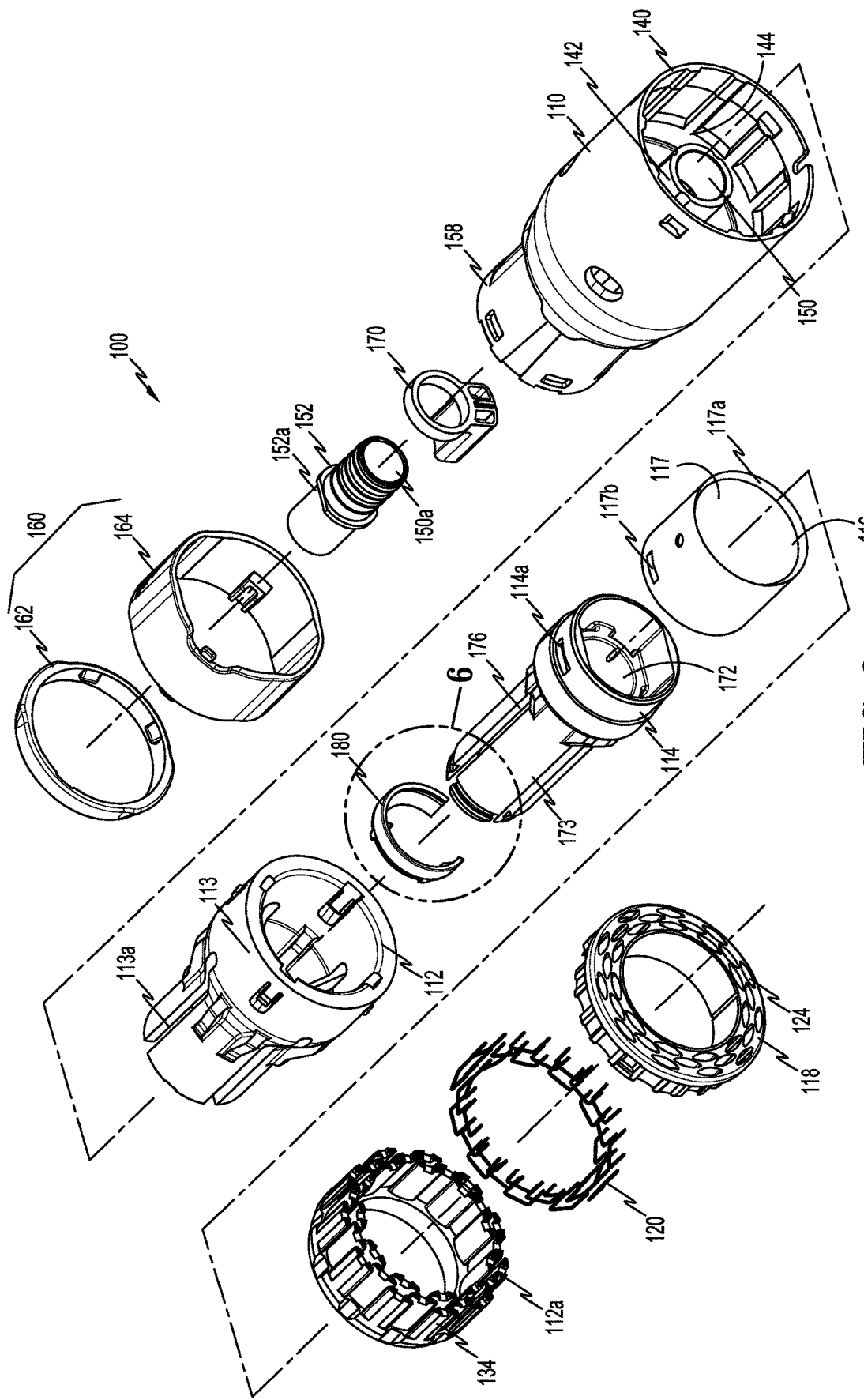
FIG. 3 is a perspective exploded view of the reload assembly shown in FIG. 2.

The disclosed reload assembly for a circular stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

FIGS. 1 and 2 illustrate a circular stapling device 10 including an exemplary embodiment of the disclosed reload assembly shown generally as a reload assembly 100. The circular stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. In embodiments, the reload assembly 100 includes a proximal portion 102 that is releasably coupled to a distal portion 14a of the adaptor assembly 14. The handle assembly 12 includes a stationary grip 22 that supports actuation buttons 24 for controlling operation of various functions of the circular stapling device 10 including approximation of the reload and anvil assemblies 100, 18, respectively, firing of staples from the reload assembly 100, and cutting or coring of tissue as described in further detail below.

The circular stapling device 10 is illustrated as an electrically powered stapling device including an electrically powered handle assembly 12 that may support one or more batteries (not shown). The adaptor assembly 14 is in the form of an adaptor assembly that translates power from the handle assembly 12 to the reload and anvil assemblies 100, 18, respectively. The adaptor assembly 14 further includes a knife carrier driver 115 (FIG. 8) that interacts with a knife carrier 114 (FIG. 3) to move the knife carrier 114 within a shell housing 110 (FIG. 3), and a staple actuator driver 195 (FIG. 8) that interacts with a staple actuator 112 (FIG. 3) to move the staple actuator 112 within the shell housing 110. Examples of electrically powered stapling devices can be found in U.S. Pat. Nos. 9,055,943, 9,023,014, and U.S. Publication Nos. 2018/0125495, and 2017/0340351. Alternately, it is envisioned that the disclosure could also be incorporated into a manually powered stapling device as disclosed in, e.g., U.S. Pat. No. 7,303,106 (the '106 Patent), or a stapling device that is configured for use with a robotic system as disclosed in, e.g., U.S. Pat. No. 9,962,159, that does not include a handle assembly. The disclosure of each of these patents and publications is incorporated by reference herein in its entirety.

FIGS. 2 and 3 illustrate the reload assembly 100 which includes the shell housing 110, the staple actuator 112, a staple pushing member 112a, the knife carrier 114, an annular knife 116 supported on the knife carrier 114, a staple cartridge 118, and a plurality of staples 120 supported within the staple cartridge 118. The staple actuator 112 includes a body 113 that is also received about the inner housing portion 142 of the shell housing 110 and is movable within the shell housing 110 from a retracted position to an advanced position. The staple cartridge 118 is annular and defines annular rows of staple pockets 124. Each of the staple pockets 124 supports one of the plurality of staples 120. The staple actuator 112 and the staple pushing member 112a together define a longitudinal through-bore 132 (FIG. 8). The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload assembly 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 112a is moved from a retracted position to an advanced position within the shell housing 110.

With particular reference to FIG. 3, the shell housing 110 includes an outer housing portion 140 and an inner housing portion 142 that are spaced from each other to define an annular cavity 144 (FIG. 3) between the outer and inner housing portions 140 and 142. The staple actuator 112 and the staple pushing member 112a are movable within the annular cavity 144 of the shell housing 110 from a retracted position to an advanced position to eject the staples 120 from the staple cartridge 118 as described in further detail below.

The annular knife 116 is supported about an outer surface of the knife carrier 114. The annular knife 116 defines a cylindrical cavity 117 and includes a distal cutting edge 117a. In embodiments, the annular knife 116 includes inwardly extending tangs 117b that are received within pockets 114a defined in an outer surface of the knife carrier 114 to secure the annular knife 116 to the knife carrier 114. The knife carrier 114 and annular knife 116 are positioned within the longitudinal through-bore 132 (FIG. 8) of the staple actuator 112 and movable from a retracted position to an advanced position to cut tissue positioned radially inward of the staple cartridge 118 as described in further detail below.

With continued reference to FIG. 3, the inner housing portion 142 of the shell housing 110 defines a through-bore 150 that receives an anvil shaft (not shown) of the anvil assembly 18. For a more detailed description of an exemplary anvil assembly 18, see, e.g., the '106 Patent. The through-bore 150 has a proximal portion that receives a bushing 152 that defines a through-bore 150a that is coaxial and forms an extension of the through-bore 150 of the inner housing portion 142. In embodiments, the bushing 152 is formed of a high strength material, e.g., metal, to provide added strength to the inner housing portion 142 of the shell housing 110 and includes an annular flange 152a.

The shell housing 110 includes a proximal portion 158 (FIG. 3) that supports a coupling mechanism 160 that is operable to releasably couple the reload assembly 100 to the adaptor assembly 14 of the circular stapling device 10 (FIG. 1) to allow for removal and replacement of the reload assembly 100 to facilitate reuse of the circular stapling device 10. The coupling mechanism 160 includes a retaining member 162 and a coupling member 164. The coupling member 164 is received about the proximal portion 158 (FIG. 3) of the shell housing 110 and is configured to engage the distal portion 14a (FIG. 1) of the adaptor assembly 14 to couple the reload assembly 100 to the adaptor assembly 14. It is envisioned that other coupling mechanisms can be used to secure the reload assembly 100 to the adaptor assembly 14. Alternatively, the reload assembly 100 can be non-removably secured to the adaptor assembly 14.

The reload assembly 100 may include an e-prom holder 170 (FIG. 3) that is supported on the shell housing 110 and is configured to support an e-prom (not shown). As is known in the art, an e-prom can communicate with the adaptor assembly 14 to provide information related to characteristics of the reload assembly 10. In some embodiments, the e-prom holder 170 can be received about a distal portion of the bushing 152.

Figure 4:
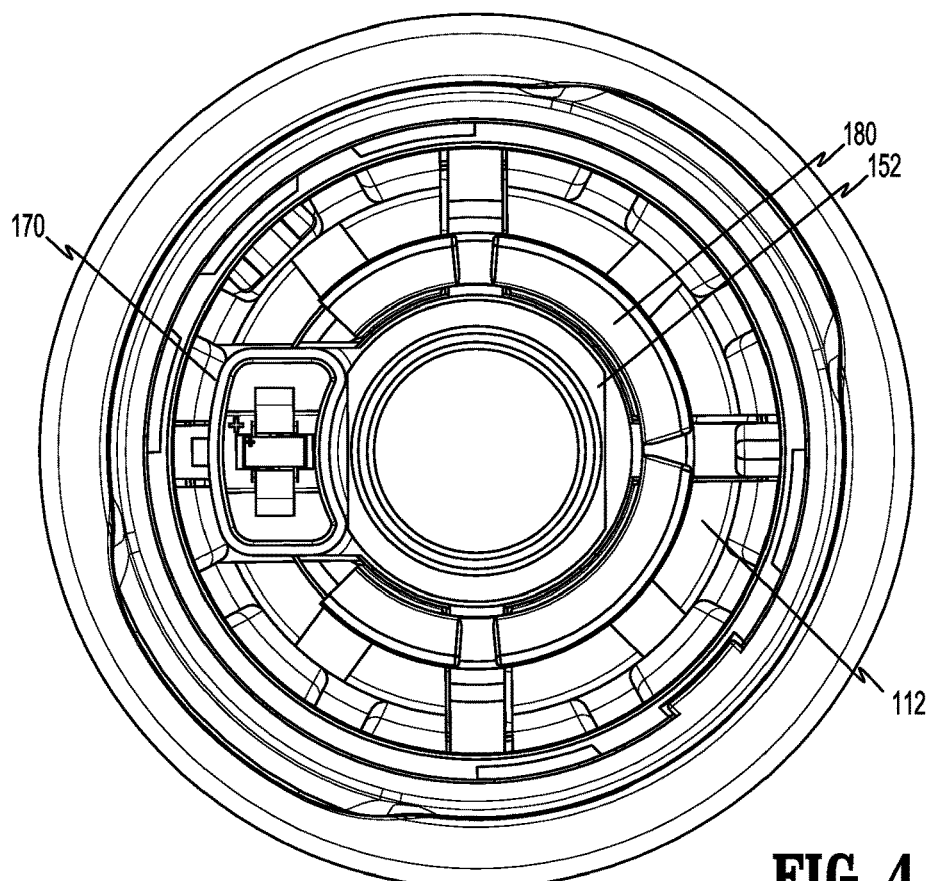
FIG. 4 is a side view of the reload assembly of the circular stapling device shown in FIG. 1.
Figure 5:
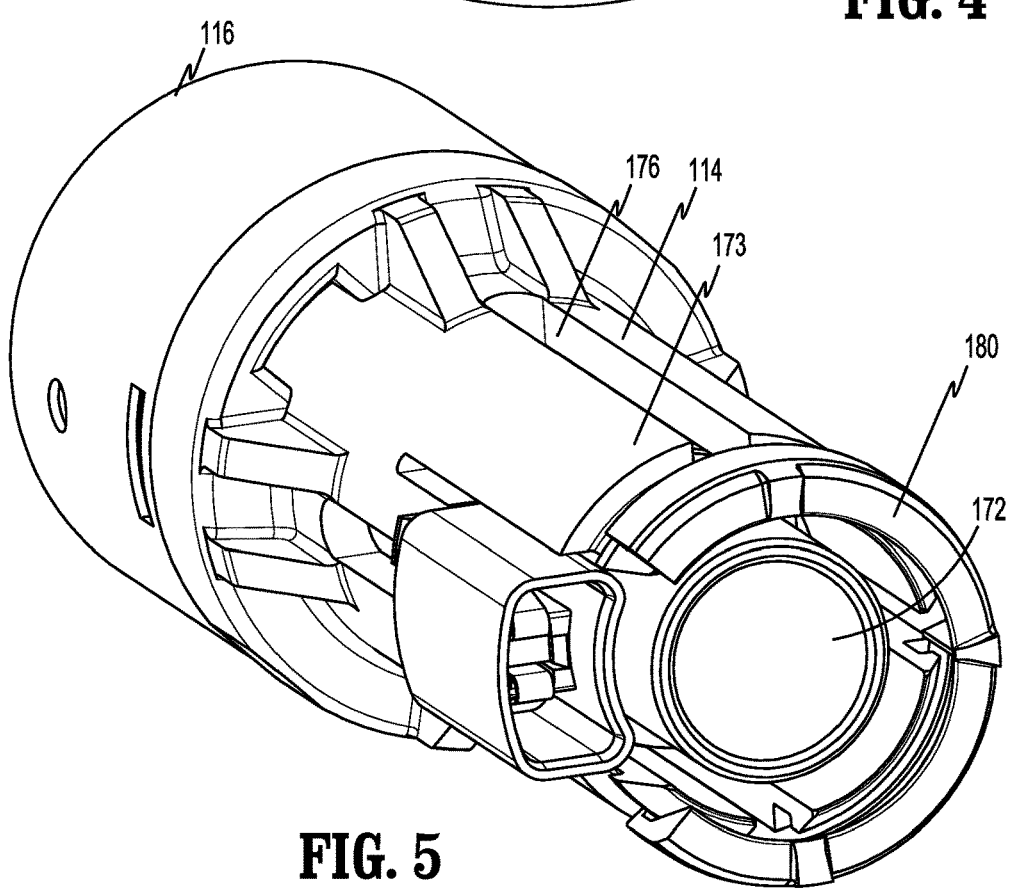
FIG. 5 is a perspective view of the reload assembly from a proximal end thereof.
Figure 14:
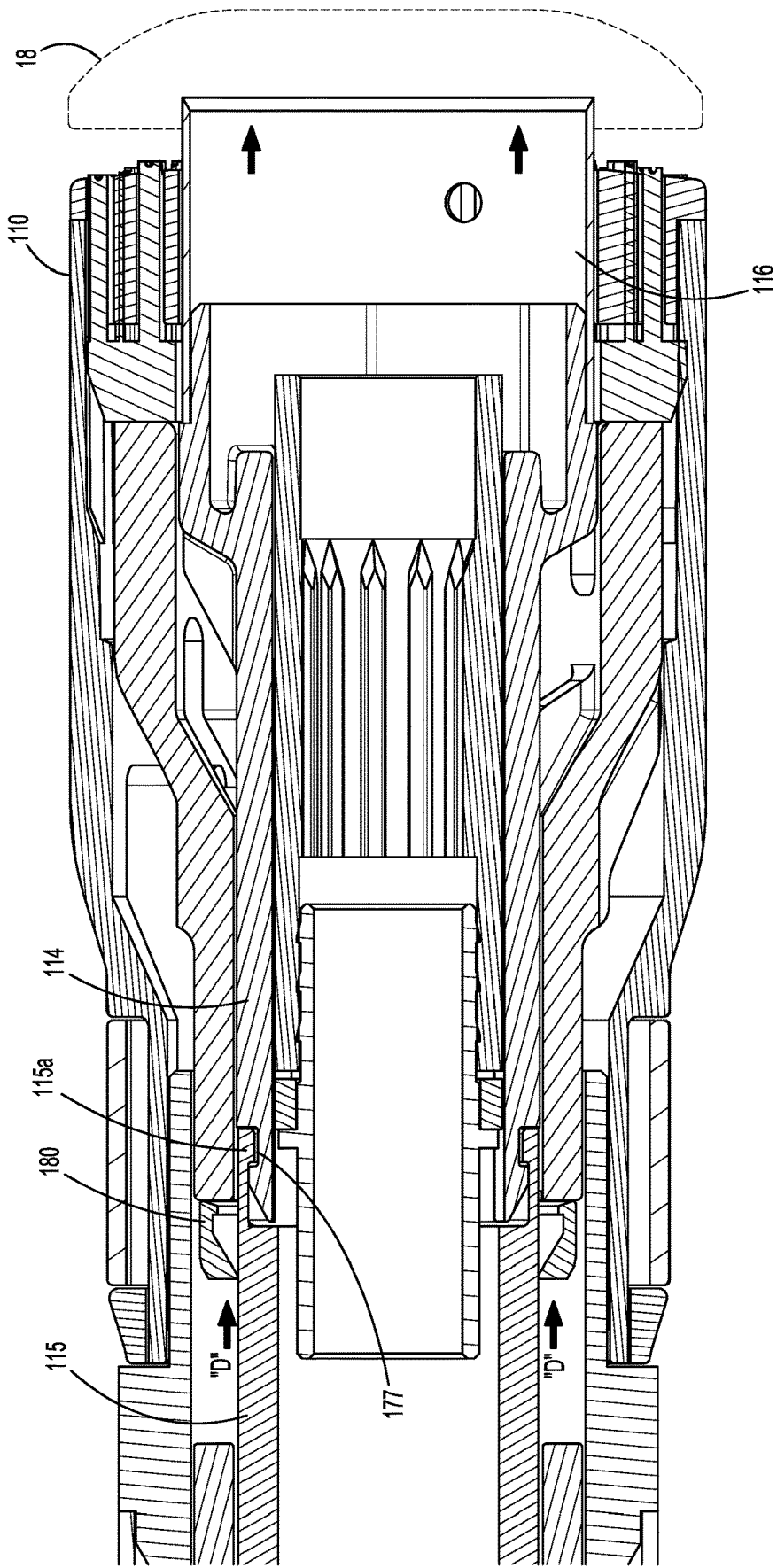
FIG. 14 is a cross-sectional view taken along section line 8-8 of FIG. 1 with the reload assembly in a fired state and the knife carrier in the advanced position.

FIGS. 3-5 illustrate the knife carrier 114 which includes a plurality of spaced longitudinally extending body portions 173 defining a central bore 172. The central bore 172 of the knife carrier 114 receives the inner housing portion 142 of the shell housing 110 such that the knife carrier 114 is movable about the inner housing portion 142 of the shell housing 110 between a retracted position (FIG. 8) and an advanced position (FIG. 14). The longitudinally extending body portions 173 of the knife carrier 114 defines slots 176 that receive guide portions (not shown) of the shell housing 110 to limit the knife carrier 114 to longitudinal movement. The knife carrier 114 includes hook members 178 (FIG. 6) that are positioned to engage the knife carrier driver 115 as described in further detail below to move the knife carrier 114 from its retracted position to its advanced position. Each of the hook members 178 includes an engagement surface 177a (FIG. 9) and supports a locking member 180. In embodiments, the locking member 180 is initially positioned adjacent or in engagement with the hook members 178. In embodiments, the locking member 180 is formed of a resilient material that can be radially deformed to be removably supported on the knife carrier 114, but is sufficiently rigid to inhibit re-advancement of the knife carrier 114 as described below.

Figure 6:
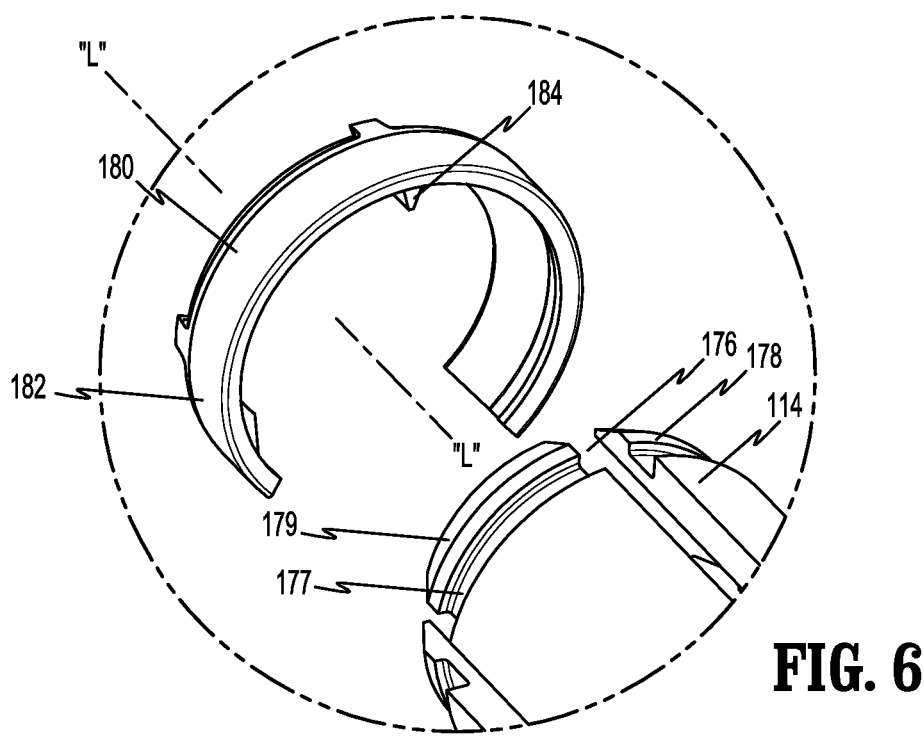
FIG. 6 is an enlarged view of the indicated area of detail shown in FIG. 3.
Figure 7:
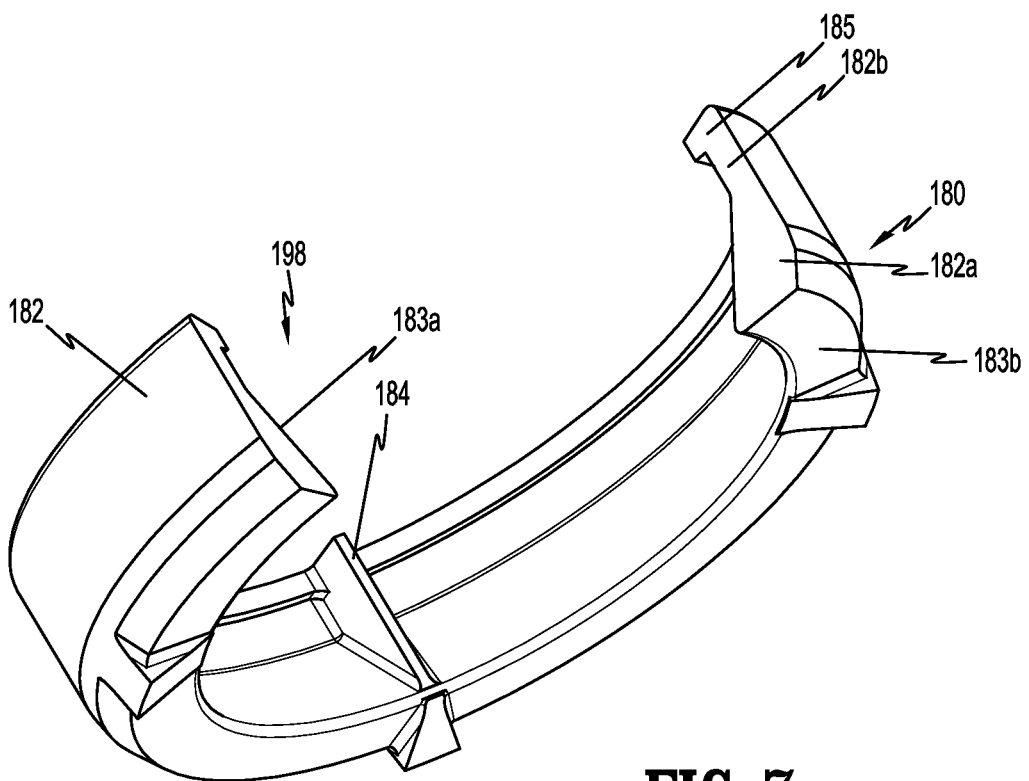
FIG. 7 is a perspective view of a locking member of the reload assembly shown in FIG. 1.

FIGS. 6 and 7 illustrate the locking member 180 of the reload assembly 100 that includes a body 182 having an annular profile. The locking member 180 is received about a proximal portion of the knife carrier 114. In particular, the locking member 180 includes at least one axial guide 184 configured to be slidably received in the slot 176 (FIG. 3) of the knife carrier 114 to inhibit rotation of the locking member 180 in relation to the knife carrier 114 in order to limit the knife carrier 114 to axial movement within the shell housing 110. In embodiments, the body 182 of the locking member 180 may define a break 198 to allow for radial flexing of the body 182 to facilitate placement of the locking member 180 in a friction fit manner about the knife carrier 114.

With continued reference to FIGS. 6 and 7, the body 182 of the locking member 180 includes a proximal portion 182a and a distal portion 182b. The proximal portion 182a includes an engaging surface 183a that extends radially inward to facilitate slidable engagement with a tapered surface 179 (FIG. 6) of the hook member 178 of the knife carrier 114. The proximal portion 182a further includes a distal surface 183b substantially orthogonal to a longitudinal axis "L-L" (FIG. 6) defined by the locking member 180. The distal surface 183b is configured to engage the engagement surface 177a (FIG. 9) of the circumferential groove 177 of the knife carrier 114. The engagement surface 177a may also be substantially orthogonal to the longitudinal axis "L-L". The distal portion 182b of the locking member 180 includes a hook portion 185 configured to be received in the circumferential groove 177 of the knife carrier 114. In addition, the hook portion 185 further include a distal surface 185a (FIG. 9) defining an acute angle with respect to the longitudinal axis "L-L" in order to enable the hook portion 185 to slide over a distal wall 177b (FIG. 9) of the circumferential groove 177 when the locking member 180 is displaced distally, as will be described below.

FIGS. 8 and 9 illustrate the staple actuator 112 which includes a body 113 that is also received about the inner housing portion 142 (FIG. 3) of the shell housing 110 and is movable from a retracted position (FIG. 8) to an advanced position (FIG. 10) in response to movement of a staple actuator driver 195 from its retracted position to its advanced position. The body 113 defines a plurality of guide slots 113a (FIG. 3). The guide slots 113a of the staple actuator 112 receive the guide members (not shown) of the shell housing 110 to limit the staple actuator 112 to longitudinal movement within the shell housing 110.

FIGS. 8 and 9 illustrate the reload assembly 100 in a pre-fired condition with the knife carrier 114 and the staple actuator 112 of the reload assembly 100 (FIG. 3) in retracted positions and the locking member 180 in an unlatched position located proximally of the distal wall 177b of the circumferential groove 177 of the knife carrier 114. When the knife carrier 114 and the staple actuator 112 are in pre-fired retracted positions, the hook portion 185 of the locking member 180 is disposed in the circumferential groove 177 of the knife carrier 114 such that the engagement surface 177a of the circumferential groove 177 is proximal of the hook portion 185 of the locking member 180. At this time, the engaging surface 183a (FIG. 7) of the locking member 180 is in an abutting relation with the tapered surface 179 (FIG. 6) of the hook member 178 of the knife carrier 114.

Figure 10:
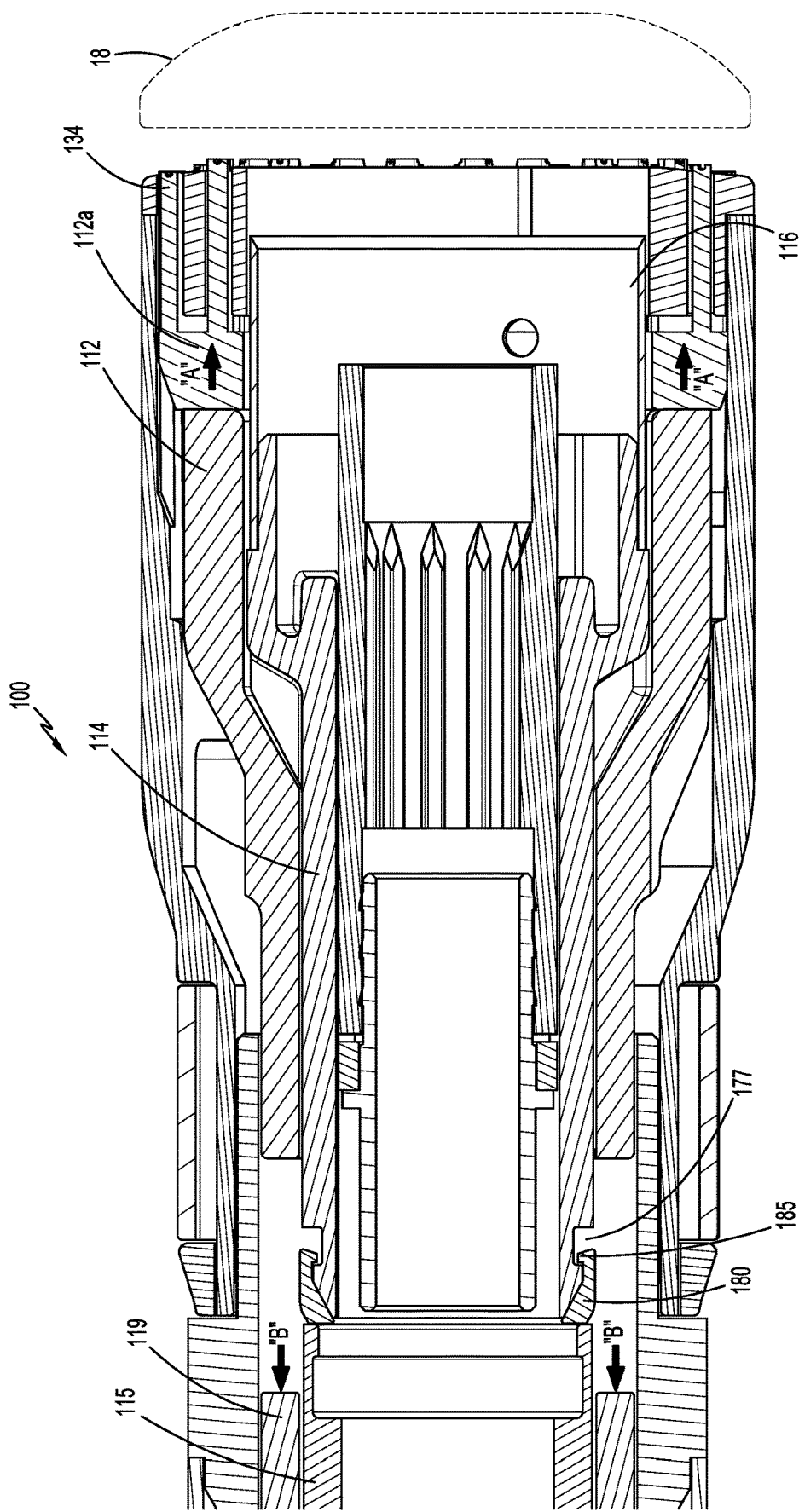
FIG. 10 is a cross-sectional view taken along section line 8-8 of FIG. 1 with the reload assembly in a fired state and a staple actuator driver in a retracted position.

FIG. 10 illustrates the reload assembly 100 as the staple actuator 112 is moved to the advanced position. As the staple actuator 112 moves distally within the shell housing 110 to the advanced position by a staple actuator driver 119, the staple pushing member 112a is moved distally in the direction indicated by arrows "A" to advance the plurality of fingers 134 of the staple pushing member 112a through the staple pockets 124 (FIG. 3) of the staple cartridge 118 to eject the staples 120 (FIG. 3) into the anvil assembly 18 (shown in phantom). As illustrated, the annular knife 116 secured to the knife carrier 114 remains stationary at this time. After the staple actuator 112 is moved to the advanced position, the staple actuator driver 119 is moved from its advanced position to its retracted position in the direction of arrows "B", while the staple actuator 112 remains in the advanced position. At this time, the engaging surface 183a (FIG. 7) of the locking member 180 remains in an abutting relation to the tapered surface 179 (FIG. 6) of the hook member 178 of the knife carrier 114, and the hook portion 185 of the locking member 180 remains within the circumferential groove 177 of the knife carrier 114.

Figure 11:
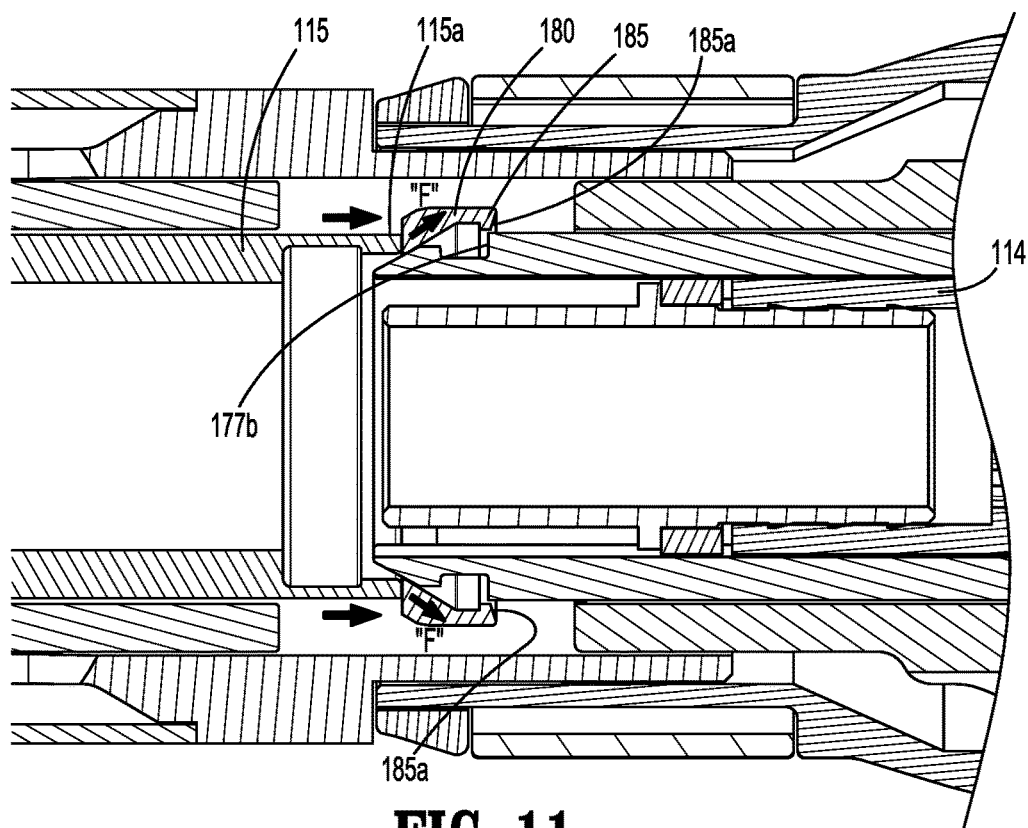
FIGS. 11 and 12 are cross-sectional views taken along section line 8-8 of FIG. 1 with the reload assembly in a fired state and a knife carrier driver moving toward its advanced position.
Figure 12:
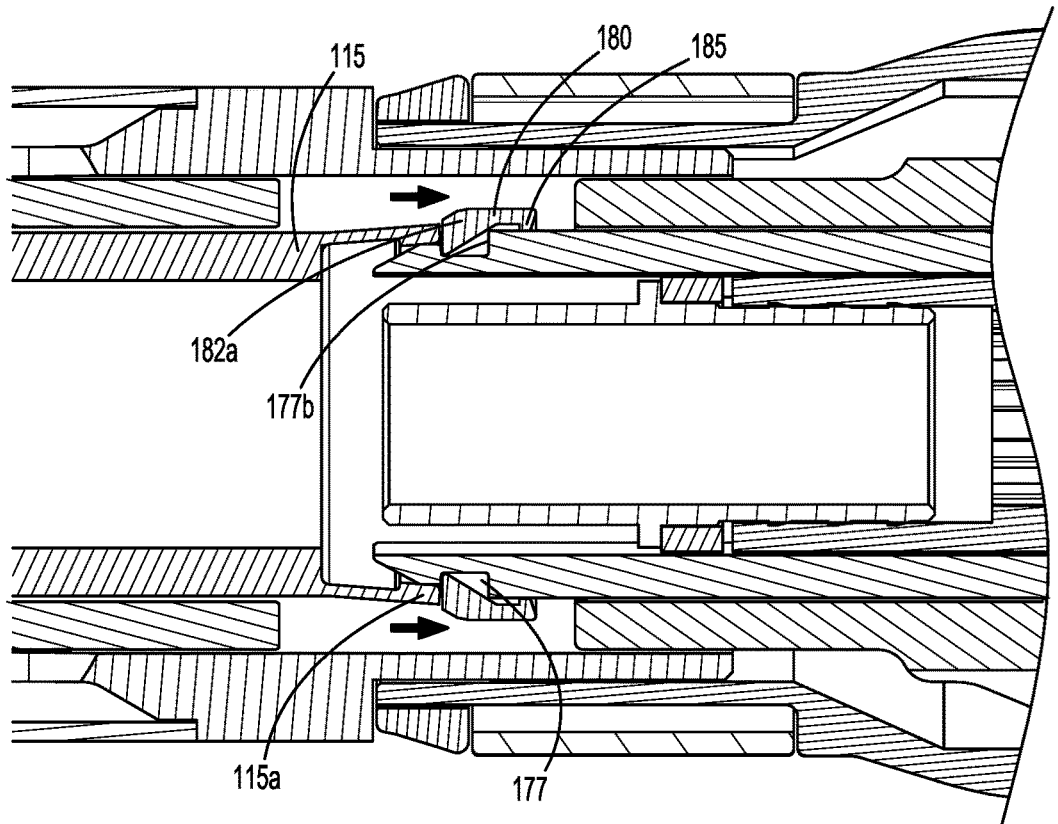

FIGS. 11 and 12 illustrate the reload assembly 100 as the knife carrier driver 115 is moved distally to advance the locking member 180 such that the engaging surface 183a (FIG. 7) of the locking member 180 slides against the tapered surface 179 (FIG. 6) of the hook member 178 of the knife carrier 114 in the direction of arrows "F" and the hook portion 185 of the locking member 180 slides over the distal wall 177b of the knife carrier 114. As discussed hereinabove, the distal surface 185a of the hook portion 185 is slanted such that when the distal surface 185a is pushed against the distal wall 177b of the knife carrier 114, the hook portion 185 slides over the distal wall 177b. As the hook portion 185 is pushed over the circumferential groove 177 of the knife carrier 114, the proximal portion 182a of the locking member 180 is placed within the circumferential groove 177.

Figure 13:
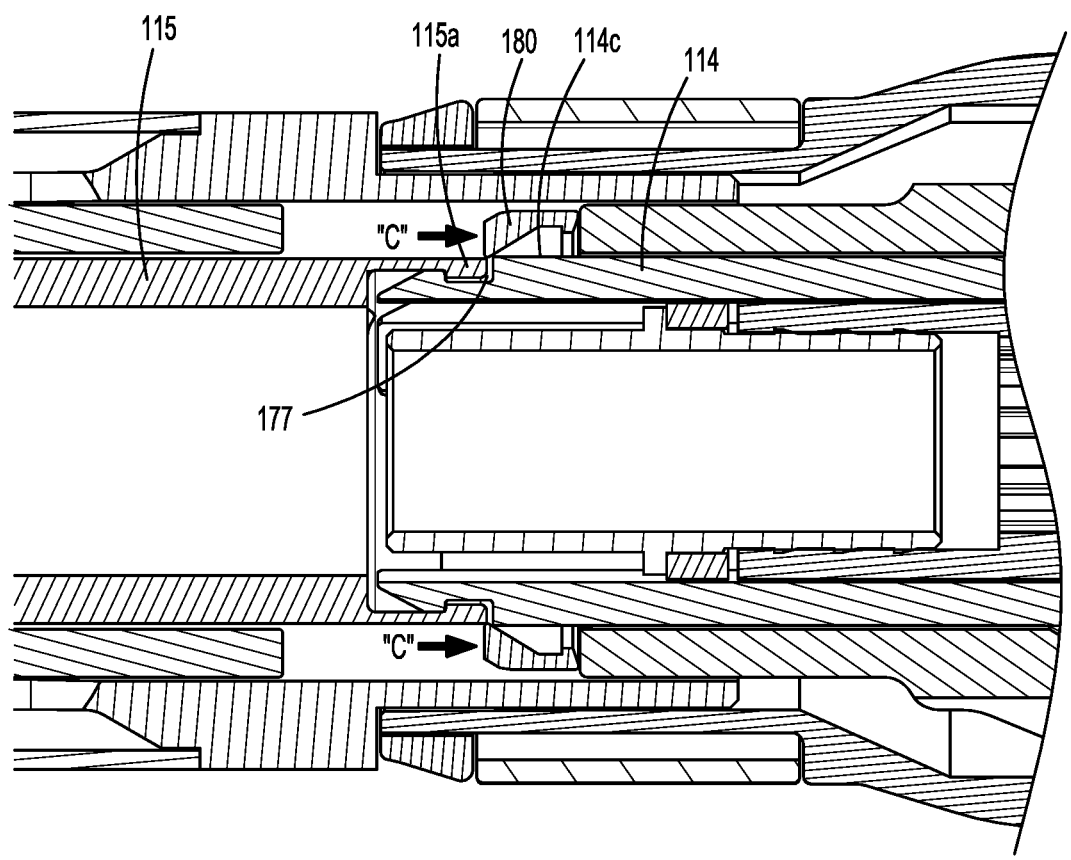
FIG. 13 is a cross-sectional view taken along section line 8-8 of FIG. 1 with the reload assembly in a fired state and the knife carrier driver moving towards the advanced position such that the knife carrier driver engages the knife carrier.

FIG. 13 illustrates the reload assembly 100 as the knife carrier driver 115 is further moved distally in the direction of arrows "C" such that the knife carrier driver 115 pushes the entire locking member 180 over the circumferential groove 177 of the knife carrier 114 to place the locking member 180 on a lateral surface 114c of the knife carrier 114. At this time, a hook portion 115a of the knife carrier driver 115 is received in the circumferential groove 177 of the knife carrier 114. Under such a configuration, distal movement of the knife carrier driver 115 is imparted to the knife carrier 114 for concomitant axial displacement.

FIG. 14 illustrates the reload assembly 100 as the knife carrier driver 115 is moved to its advanced position. When the knife carrier driver 115 is moved to the advanced position, the axial displacement of the knife carrier driver 115 is imparted to the knife carrier 114 which, in turn, advances the annular knife 116 out of the shell housing 110 and into engagement with the anvil 18 (shown in phantom) to cut tissue. At this time, the hook portion 115a of the knife carrier driver 115 disposed within the circumferential groove 177 of the knife carrier 114 is disposed distal of the locking member 180.

Figure 15:
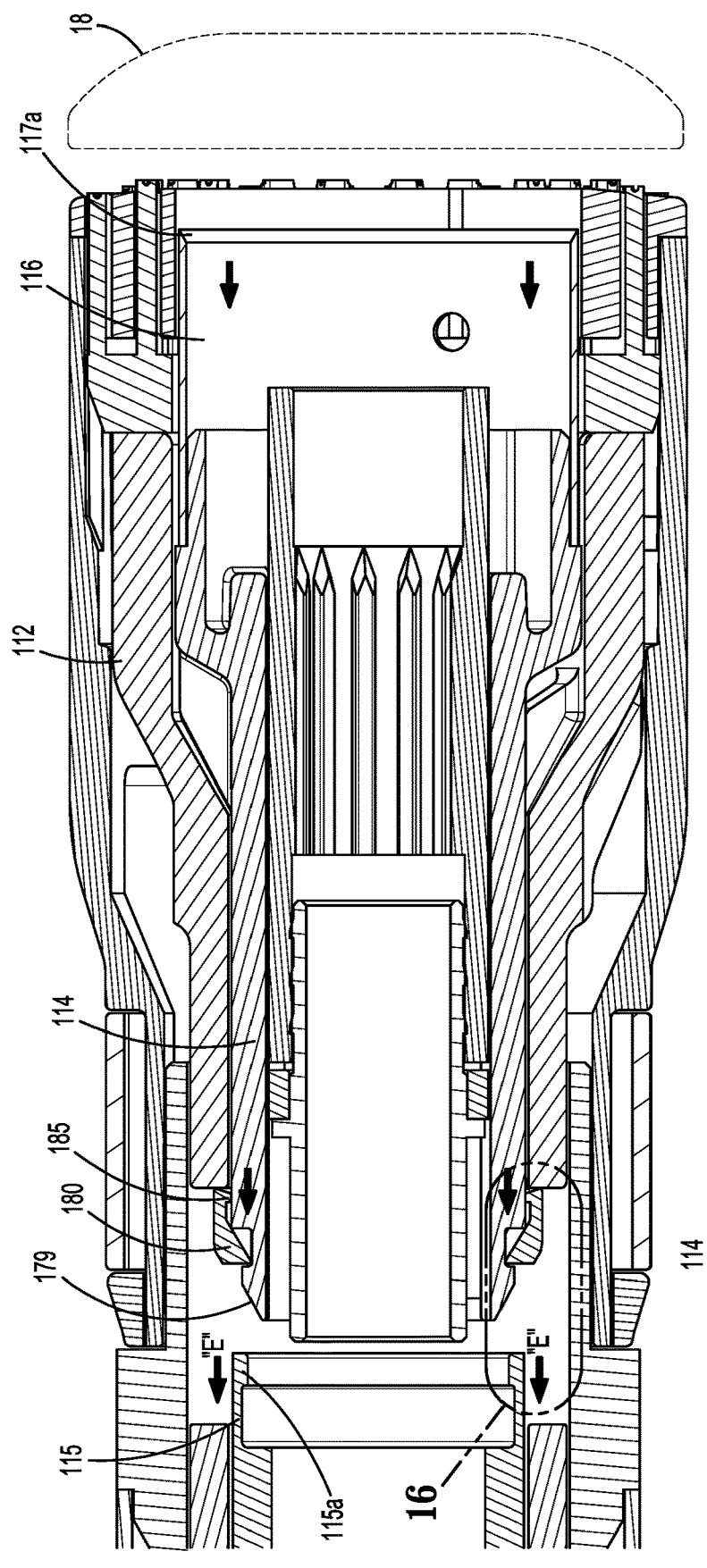
FIG. 15 is a cross-sectional view taken along section line 8-8 of FIG. 1 with the reload assembly in a fired state and the knife carrier in a locked position by a locking member.
Figure 16:
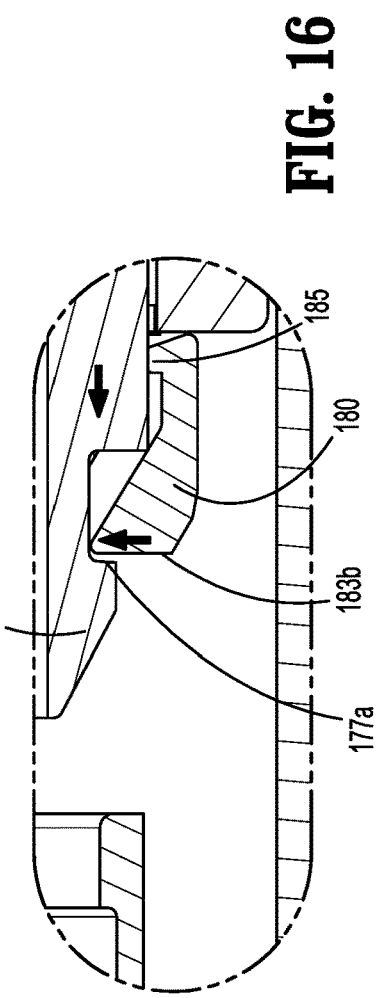
FIG. 16 is an enlarged view of the indicated area of detail shown in FIG. 15.

FIGS. 15 and 16 illustrate the reload assembly 100 as the knife carrier 114 is moved from its advanced position to its retracted position after the reload assembly is fired. When the knife carrier 114 is moved proximally in the direction indicated by arrows "E" towards its retracted position, the annular knife 116 is also moved proximally to a position located within the shell housing 110. In this position, a clinician is protected from inadvertent injury caused by the cutting edge 117a of the annular knife 116. As the knife carrier 114 moves proximally in relation to the staple actuator 112, the hook portion 115a of the knife carrier driver 115 disposed in the circumferential groove 177 of the knife carrier 114 is also displaced proximally until the hook portion 115a is placed in registration with the hook portion 185 of the locking member 180. At this time, the hook portion 185 of the locking member 180 applies inward pressure to the hook portion 115a of the knife carrier driver 115 to relieve the hook portion 115a from the circumferential groove 177 of the knife carrier 114. In particular, as the hook portion 185 of the locking member 180 applies inward pressure to the hook portion 115a of the knife carrier driver 115, a proximal portion of the hook portion 115a bends radially outward to enable the hook portion 115a to slide over the engagement surface 177a of the circumferential groove 177, which allows the knife carrier driver 115 to disengage from the knife carrier 114 when the knife carrier driver 115 is proximally displaced. In this manner, the knife carrier 114 is in the retracted position and the knife carrier driver 115 is displaced away from the knife carrier 114. At this time, the locking member 180 is anchored against the circumferential groove 177 of the knife carrier 114 and the staple actuator 112 to inhibit exposure of the annular knife 116 out of the shell housing 110 by inadvertent actuation of the knife carrier 114. Under such a configuration, the locking member 180 engages the staple actuator 112 in the advanced position such that even when the knife carrier diver 115 is inadvertently actuated, the locking member 180 inhibits transition of the knife carrier 114 to the advanced position. In particular, the hook portion 115a of the knife carrier driver 115 is inhibited from being received in the circumferential groove 177 of the knife carrier 114, thereby inhibiting axial displacement of the knife carrier 114 by the knife carrier driver 115. Once again, this obstructs advancement of the knife carrier 114 to inhibit re-advancement of the annular knife 116 from within the shell housing 110.

As an alternative to the handle assembly 12 (FIG. 1) configured for manual grasping and manipulation during use, the circular stapling device 10 may alternatively be configured for use with a robotic surgical system wherein the reload assembly 100 is configured to engage a robotic arm of the robotic surgical system in a similar manner as detailed above with respect to engagement of the reload assembly 100 with the adaptor assembly 14. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
    an adaptor assembly having a proximal end portion and a distal end portion; and
    a reload assembly supported on the distal end portion of the adaptor assembly, the reload assembly including:
        a shell housing including an outer housing portion and an inner housing portion, the inner and outer housing portions defining an annular cavity;
        a staple cartridge supporting a plurality of staples;
        a staple pusher supported within the annular cavity and movable from a retracted position to an advanced position to eject the plurality of staples from the staple cartridge;
        a staple actuator supported within the annular cavity and movable from a retracted position to an advanced position to move the staple pusher from its retracted position to its advanced position;
        a knife carrier supported within a through bore and movable between a retracted position and an advanced position, the knife carrier supporting a knife; and
        a locking member slidably supported on the knife carrier, the locking member configured to engage the staple actuator in its advanced position while engaging the knife carrier in its retracted position such that the locking member inhibits re-advancement of the knife carrier.

2. The surgical stapling device according to claim 1, wherein the knife carrier has a proximal portion defining a circumferential groove configured to anchor the locking member thereagainst, when the locking member engages the staple actuator is in its advanced position.

3. The surgical stapling device according to claim 1, wherein the locking member has an annular profile.

4. The surgical stapling device according to claim 1, wherein the locking member has a break for radial flexing thereof.

5. The surgical stapling device according to claim 1, wherein the locking member includes proximal and distal portions, the proximal portion having an engaging surface extending radially inward and a proximal surface defining an acute angle with the engaging surface.

6. The surgical stapling device according to claim 5, wherein the distal portion of the locking member includes a hook portion.

7. The surgical stapling device according to claim 6, wherein the knife carrier includes a plurality of longitudinally extending body portions, wherein adjacent longitudinally extending body portions defines a slot.

8. The surgical stapling device according to claim 7, wherein the locking member includes an axial guide configured to be slidably received in the slot of the knife carrier.

9. The surgical stapling device according to claim 7, wherein each longitudinally extending body portion includes a proximal portion defining a groove and a tapered portion proximal of the groove.

10. The surgical stapling device according to claim 9, wherein the tapered portion of the longitudinally extending body portion is configured to slidably engage the engaging surface of the locking member.

11. The surgical stapling device according to claim 9, wherein the groove of the knife carrier includes a distal wall and a proximal wall, the hook portion of the locking member includes an engaging surface configured to slide over the distal wall of the groove.

12. The surgical stapling device according to claim 11, wherein the proximal surface of the locking member is configured to engage the proximal wall of the groove when the locking member engages the staple actuator in its advanced position.

13. A surgical stapling device comprising:
    a reload assembly including:
        a shell housing defining an annular cavity;
        a staple cartridge supporting a plurality of staples;
        a staple pusher supported within the annular cavity and movable from a retracted position to an advanced position to eject the plurality of staples from the staple cartridge;
        a staple actuator supported within the annular cavity and engaged with the staple pusher, the staple actuator movable from a retracted position to an advanced position to move the staple pusher from its retracted position to its advanced position, the staple actuator and the staple pusher defining a through bore;
a knife carrier supported within the through bore and movable between a retracted position and an advanced position, the knife carrier including a proximal portion defining a notch, the knife carrier supporting a knife; and
a locking member slidably supported on the knife carrier, the locking member including an annular body having a proximal end configured to be anchored against the notch of the knife carrier and a distal end configured to engage the staple actuator such that when the staple actuator is in its advanced position and the knife carrier is in its retracted position, the locking member inhibits re-advancement of the knife carrier.

14. The surgical stapling device according to claim 13, wherein the locking member defines a break for radial flexing thereof.

15. The surgical stapling device according to claim 13, wherein a distal end of the locking member is configured to slide over the notch of the knife carrier.

16. The surgical stapling device according to claim 15, wherein the locking member includes axial guide configured to limit the locking member to an axial movement relative to the knife carrier.

17. The surgical stapling device according to claim 15, wherein the proximal end of the locking member includes an engaging surface extending radially inward, the engaging surface configured to slidably engage a tapered portion of the proximal portion of the knife carrier.

18. The surgical stapling device according to claim 13, wherein the distal end of the locking member includes a hook portion.

19. The surgical stapling device according to claim 18, wherein the distal end of the hook portion is tapered.

* * * * *